United States Patent
Smith et al.

(10) Patent No.: US 8,750,561 B2
(45) Date of Patent: Jun. 10, 2014

(54) METHOD OF DETECTING MATERIAL IN A PART

(75) Inventors: Kevin D. Smith, Glastonbury, CT (US); Jeffrey A. Umbach, Palm Beach Garden, FL (US)

(73) Assignee: United Technologies Corporation, Hartford, CT (US)

( * ) Notice: Subject to any disclaimer, the term of this patent is extended or adjusted under 35 U.S.C. 154(b) by 184 days.

(21) Appl. No.: 13/408,346

(22) Filed: Feb. 29, 2012

(65) Prior Publication Data

US 2013/0223672 A1   Aug. 29, 2013

(51) Int. Cl.
*G06K 9/00* (2006.01)

(52) U.S. Cl.
USPC .......................................................... 382/100

(58) Field of Classification Search
USPC ................................... 382/100, 254; 702/40
See application file for complete search history.

(56) References Cited

U.S. PATENT DOCUMENTS

| | | | |
|---|---|---|---|
| 3,418,467 A | | 12/1968 | Spielberg et al. |
| 3,624,397 A | | 11/1971 | Honeycutt et al. |
| 4,561,054 A | * | 12/1985 | Andrews et al. ............... 600/407 |
| 5,242,007 A | | 9/1993 | Remmers et al. |
| 5,489,781 A | | 2/1996 | Mohr et al. |
| 5,519,225 A | | 5/1996 | Mohr et al. |
| 6,889,707 B2 | | 5/2005 | Nicolino |
| 6,923,206 B2 | | 8/2005 | Glover et al. |
| 6,929,023 B2 | | 8/2005 | Whitaker et al. |
| 7,191,795 B2 | | 3/2007 | Hettmann et al. |
| 7,218,706 B2 | | 5/2007 | Hopkins et al. |
| 7,331,359 B2 | | 2/2008 | Shay |
| 7,441,585 B2 | | 10/2008 | Otero et al. |
| 7,654,283 B2 | | 2/2010 | Seto et al. |
| 7,814,931 B2 | | 10/2010 | Newton et al. |
| 2002/0057760 A1 | * | 5/2002 | Carroll et al. ................. 378/119 |
| 2004/0176677 A1 | | 9/2004 | Hwu et al. |
| 2005/0091848 A1 | | 5/2005 | Nenov et al. |
| 2005/0147851 A1 | * | 7/2005 | Fujioka et al. ................ 428/698 |
| 2008/0240531 A1 | | 10/2008 | Sasaki et al. |
| 2009/0257552 A1 | | 10/2009 | Warner et al. |
| 2009/0272908 A1 | | 11/2009 | Warner et al. |
| 2009/0316853 A1 | | 12/2009 | Parazzoli et al. |
| 2013/0039472 A1 | * | 2/2013 | Morton ........................... 378/88 |

FOREIGN PATENT DOCUMENTS

| | | |
|---|---|---|
| EP | 0105126 A2 | 4/1984 |
| KR | 100608225 B1 | 8/2006 |
| WO | 0213908 A2 | 2/2002 |

OTHER PUBLICATIONS

International Search Report and Written Opinion for International Application No. PCT/US2013/027585 completed Jun. 19, 2013.

* cited by examiner

*Primary Examiner* — Gregory F Cunningham
(74) *Attorney, Agent, or Firm* — Carlson, Gaskey & Olds, PC

(57) ABSTRACT

A method includes the steps of producing a first digital x-ray image of a part utilizing a full energy spectrum, producing a second digital x-ray image of the part with a hardened beam correlating to a higher energy portion of the full energy spectrum, subtracting the second x-ray image from the first x-ray image, and using a remainder of the subtracting step to locate the matter.

20 Claims, 2 Drawing Sheets

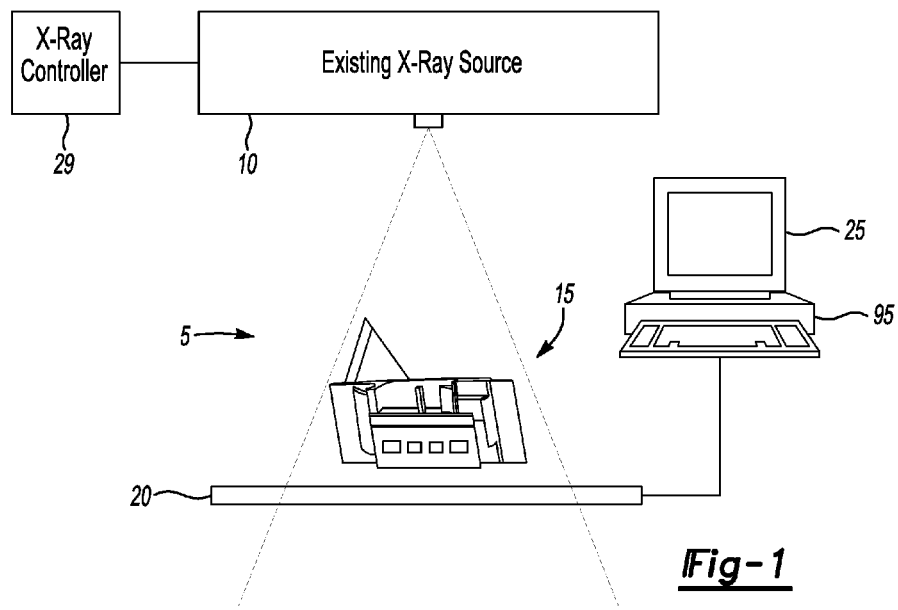
*Fig-1*
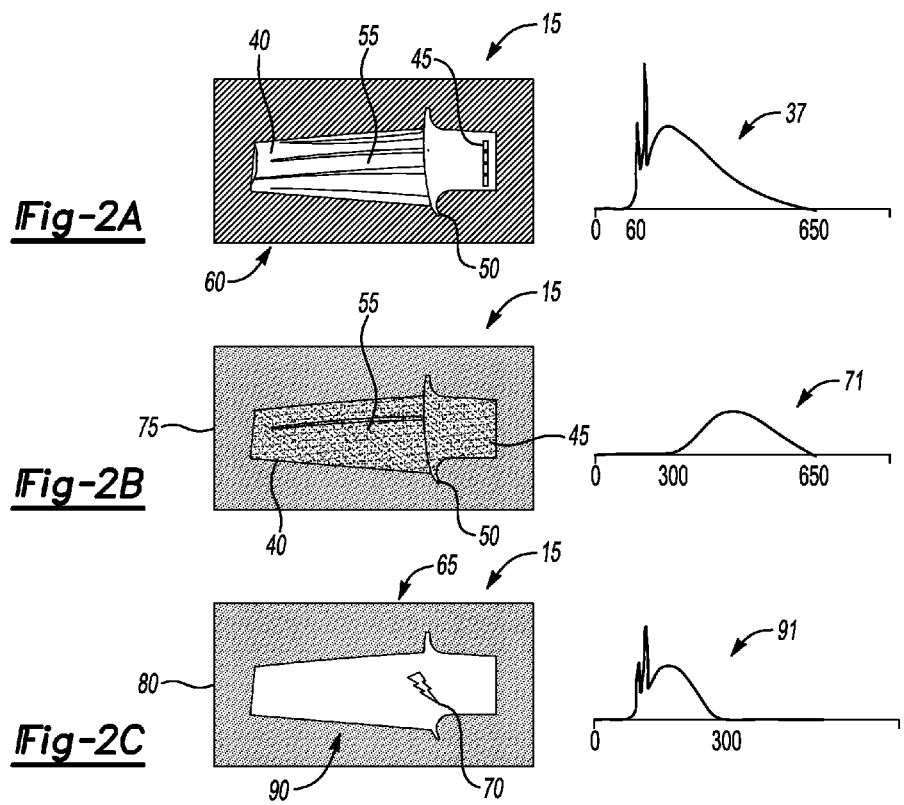
*Fig-2A*
*Fig-2B*
*Fig-2C*

METHOD OF DETECTING MATERIAL IN A PART

BACKGROUND

Detection of materials that are present within another material using x-rays is particularly difficult if the surrounding material has a significantly higher x-ray absorption characteristic. For such cases, higher x-ray energies are required to penetrate and evaluate the surrounding material which can make the materials with low absorption characteristics essentially invisible in the resulting x-ray image.

An example of such a case is the detection of casting core material within the metal structure of aerospace components. While the core material is intended to be completely removed before part usage, a costly neutron radiographic procedure is typically invoked to detect residual core material that would be detrimental to the part if left in the part.

There is a need to be able to detect the presence of material with low x-ray absorption characteristics in the presence of material with high x-ray absorption characteristic in a timely and cost effective manner. In particular, using the method for detection of low x-ray absorption material in conjunction with x-ray inspections already used for inspection of other characteristics of the component such as the presence of voids would provide an especially efficient inspection process.

SUMMARY

An exemplary method disclosed herein includes the steps of producing a first digital x-ray image of a part utilizing a full x-ray spectrum, producing a second digital x-ray image of the part utilizing a higher energy portion of the full spectrum, subtracting the second x-ray image from the first x-ray image, and using a remainder of the subtracting step to locate certain matter.

In another embodiment of the exemplary method of any of the preceding paragraphs, the method includes creating a first digital x-ray image of the part.

In another embodiment of the exemplary method of any of the preceding paragraphs, the method includes creating a second digital x-ray image of the part.

In another embodiment of the exemplary method of any of the preceding paragraphs, the method includes creating a third digital x-ray image of the part.

In another embodiment of the exemplary method of any of the preceding paragraphs, the method includes enhancing the remainder for detection by a user or through automated algorithms, of the matter.

In another embodiment of the exemplary method of any of the preceding paragraphs, the method includes creating an image of the remainder in which the matter is displayed.

In another embodiment of the exemplary method of any of the preceding paragraphs, the method includes a limitation wherein the part is in a same position during the x-raying steps.

A further exemplary method disclosed herein includes the steps of producing a first digital x-ray image of a blade utilizing a full x-ray spectrum, producing a second digital x-ray image of the blade with a hardened beam correlating to an upper portion of the full spectrum, subtracting the second x-ray image from the first x-ray image, and using a remainder of the subtracting step to locate matter.

In another embodiment of the exemplary method of any of the preceding paragraphs, the method includes the limitation the full spectrum is between 60-650 Kv.

In another embodiment of the exemplary method of any of the preceding paragraphs, the method includes the limitation wherein the hardened beam is between 300-650 Kv.

In another embodiment of the exemplary method of any of the preceding paragraphs, the producing a first x-ray step includes creating a first image of the x-rayed part, the producing a second x-ray step includes creating a second image of the x-rayed part and the subtraction step includes creating a third image of the x-rayed part.

In another embodiment of the exemplary method of any of the preceding paragraphs, the method includes enhancing the remainder for detection by a user or through automated algorithms, of the matter.

In another embodiment of the exemplary method of any of the preceding paragraphs, the method includes creating an image of the remainder in which the matter is displayed.

In another embodiment of the exemplary method of any of the preceding paragraphs, the method includes a limitation wherein the part is in a same position during the x-raying steps.

A still further exemplary method disclosed herein includes the steps of producing a first digital x-ray image of a blade across a full spectrum, producing a second x-ray of the blade with a hardened beam correlating to an upper portion of the full spectrum, subtracting the second x-ray from the first digital x-ray image, and using a remainder of the subtracting step to locate matter.

In another embodiment of the exemplary method of any of the preceding paragraphs, the method includes a limitation wherein the full spectrum is between 60-650 Kv and a hardened beam is between 300-650 Kv.

In another embodiment of the exemplary method of any of the preceding paragraphs, the method includes enhancing the remainder for detection by a user or through automated algorithms, of the matter.

In another embodiment of the exemplary method of any of the preceding paragraphs, the method includes a limitation wherein the producing a first x-ray step includes creating a first digital image of the x-rayed part, the producing a second x-ray step includes creating a second digital image of the x-rayed part and the subtraction step includes creating a third digital image of the x-rayed part.

BRIEF DESCRIPTION OF THE DRAWINGS

The various features and advantages of the present disclosure will become apparent to those skilled in the art from the following detailed description. The drawings that accompany the detailed description can be briefly described as follows.

FIG. 1 shows an apparatus for x-raying a part.

FIG. 2A shows a first x-ray image of a blade with a first x-ray spectrum using the apparatus of FIG. 1.

FIG. 2B shows a second x-ray image of a blade with a second, overlapping second x-ray spectrum using the apparatus of FIG. 1.

FIG. 2C shows a view of the part wherein the second x-ray image is subtracted from the first x-ray image using the apparatus of FIG. 1.

DETAILED DESCRIPTION OF THE PREFERRED EMBODIMENT

Figure 3:
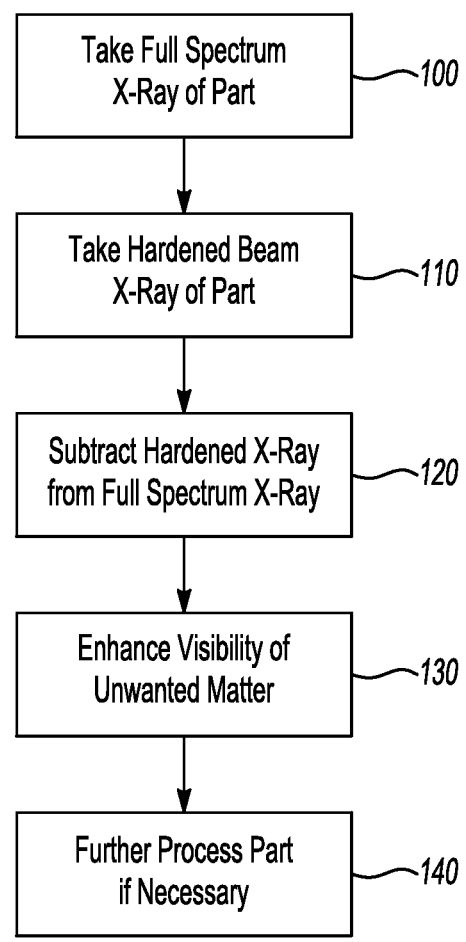
FIG. 3 shows a method of detecting matter in a part using the apparatus of FIG. 1.

Referring now to FIG. 1, an x-ray system 5, includes an x-ray source 10, as is known in the art, a part (such as a blade 15) to be x-rayed and a digital x-ray detector 20. The x-ray detector 20 is connected to a general purpose computer 25 which receives information from the digital x-ray detector 20. The x-ray source is driven by a controller 29.

Referring now to FIGS. 2A, 2B, 2C, the blade 15 may be used in the turbine environment in a gas turbine engine (not shown). The blade 15 has an airfoil 40, a base 45, a platform 50 and an air passage 55. Referring to FIG. 2A, a first image 60 of an x-ray of the blade 15 is displayed including its airfoil 40, base 45, platform 50 and the air passage 55. The blade 15 may be made as noted above of titanium or nickel alloys or the like. For an exemplar, the blade 15 shown herein is made of a nickel alloy.

FIG. 2A shows a first image 60 created in a first plurality of pixels (not shown) in which the x-ray source 10 bombards the blade 15 with a full spectrum of energy between 60 and 650 kilovolts ("Kv") as shown in graph 37. The data that is recorded at the detector exemplifies the absorption characteristics of the unwanted material as well as the parent material of the blade 15. The resultant image, however, is overwhelmed by the highly attenuative parent material. For instance, one can see the main elements of the blade 15 including the airfoil 40, the base 45, the platform 50 and the air passage 55. The first image 60 forms a first part 100 (see FIG. 3) of the process. One of ordinary skill in the art will recognize that other full spectrum energy levels may be required for different materials, or for thicker or thinner portions of other parts 15.

In image 60 of FIG. 2A, one cannot see any foreign material or defects 70 (see residual ceramic core particles 70 in FIG. 2C) very well. Such material or defect 70 may also be disposed in the blade 15 and may include dross or other low density particles, porosity, micro-shrinkage, grain boundary separation, or the like.

As a second part 110 (see FIG. 3) of the process and as shown in FIG. 2B, a hardened beam (e.g., a spectrum between 300 to 650 Kv or a higher range of the full spectrum of energy—see graph 71) is used to bombard the part 15 to create second image 75, typically with the same plurality of pixels (not shown). By using such higher energy, a second image 75 is shown of the structure of the blade 15, including the airfoil 40, the base 45, the platform 50 and the air passage 55. One of ordinary skill in the art will recognize that other hardened beams having different ranges of energy may be required to be used for different materials, or for thicker or thinner portions of other parts 15. One should also note that the first image 60 and the second image 75 is taken while the part 15 is in the same position. There are no registration issues of the two images 60, 75 thereby.

To reveal the material 70, as a third part 120 (see FIG. 3) of the process, a third image 80 (see FIG. 2C) is created to allow the material 65 to be seen. The second image 75 is subtracted from the first image 60 on a pixel-by-pixel basis within the general purpose computer 25. The pixels that display in FIG. 2C are essentially the remainder of the subtraction step 120. As shown in graph 91 of FIG. 2C, the spectrum shown relates to the energy in the 60-300 Kv range.

As a fourth part 130 (see FIG. 3) of the process, the computer processes the third image 80 to enhance an image 90 of the matter 70 by using an automated algorithm 95 as is known in the art residing in general purpose computer 25. As known in the art, the computer 25 in conjunction with the x-ray detector 20 captures a number of counts of x-rays strikes in a pixel of the x-ray detector that relate to each portion of the part 15 as the part is bombarded over a given period of time. The unwanted matter 70 is not easily seen in the full x-ray spectrum image because the image is overwhelmed by the denser materials shown in FIGS. 2A and 2B. Yet after the subtraction of the second image 75 from the first image 60, the effects of the blade geometry can be eliminated (see FIG. 2C and graph 91). The unwanted matter 70 also may not show, without enhancement, if a full spectrum x-ray between 60 and 300 kilovolts is taken because the image data is overwhelmed by the attenuation characteristic of part 15.

As a fifth part 140 (see FIG. 3) of the process, the part 15 such as blade 15 may be scrapped, repaired or reprocessed depending on the severity of the unwanted matter or defect 65 present.

One of ordinary skill in the art will recognize that this process may be used in determining the presence of material that does not belong in an environment, such as the human body, or other bodies where harder materials that attenuate more may exist, e.g., as a stent. This process may require more exact manipulation of the breadth of the full x-ray spectrum and the hardened beams to allow for unwanted material to be seen. One of ordinary skill in the art will recognize that, while two dimensional images 60, 75 and 80 are shown herein, as technology advances, more than two dimensional images may be created and use the teachings herein.

Although a combination of features is shown in the illustrated examples, not all of them need to be combined to realize the benefits of various embodiments of this disclosure. In other words, a system designed according to an embodiment of this disclosure will not necessarily include all of the features shown in any one of the Figures or all of the portions schematically shown in the Figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A method for detecting matter in a part comprises the steps of:
    producing a first x-ray image of a part utilizing a full energy spectrum,
    producing a second x-ray image of said part utilizing a beam correlating to a higher energy portion of said full spectrum,
    subtracting said second x-ray image from said first x-ray image, and
    using a remainder of said subtracting step to locate the matter, and wherein said matter is residual ceramic core particles, and said part is a metallic part.

2. The method of claim 1 wherein said producing a first x-ray image step includes creating a first image of said x-rayed part.

3. The method of claim 2 wherein said producing a second x-ray image step includes creating a second image of said x-rayed part.

4. The method of claim 3 wherein said subtraction step includes creating a third image of said x-rayed part.

5. The method of claim 1 further comprising:
    enhancing said remainder for detection by a user or through automated algorithms of said matter.

6. The method of claim 1 further comprising:
    creating an image of said remainder in which said matter is displayed.

7. The method of claim 6 further comprising:
    enhancing said remainder for detection by a user or through automated algorithms of said matter.

8. The method of claim 1 wherein said part is in a same position during said x-raying steps.

9. A method for detecting matter relating to an airfoil comprises the steps of:
producing a first x-ray image of a blade utilizing a full energy spectrum,
producing a second x-ray of said blade with a hardened beam correlating to a higher energy portion of said full spectrum, said hardened beam is between 300-650 Kv,
subtracting said second x-ray image from said first x-ray image, and
using a remainder of said subtracting step to locate the matter.

10. The method of claim 9 wherein said full spectrum is between 60-650 Kv.

11. The method of claim 9 wherein said producing a first x-ray step includes creating a first image of said x-rayed airfoil, said producing a second x-ray step includes creating a second image of said x-rayed airfoil and said subtraction step includes creating a third image of said x-rayed airfoil.

12. The method of claim 9 further comprising:
enhancing said remainder for detection by a user or through automated algorithms of said matter.

13. The method of claim 9 further comprising:
creating an image of said remainder in which said matter is displayed.

14. The method of claim 13 further comprising:
enhancing said remainder for detection by a user or through automated algorithms of said matter.

15. The method of claim 9 wherein said airfoil is in a same position during said x-raying steps.

16. A method for detecting unwanted matter relating to a blade for a gas turbine engine comprises the steps of:
producing a first x-ray image of a blade utilizing a full energy spectrum,
said full spectrum is between 60-650 Kv and said hardened beam is between 300-650 Kv
producing a second x-ray image of said blade with a hardened beam correlating to a higher energy portion of said full spectrum,
subtracting said second x-ray from said first x-ray, and
using a remainder of said subtracting step to locate the matter.

17. The method of claim 16 further comprising
enhancing said remainder for detection by a user or through automated algorithms of said matter.

18. The method of claim 16 wherein said producing a first x-ray image step includes creating a first image of said x-rayed blade, said producing a second x-ray image step includes creating a second image of said x-rayed blade and said subtraction step includes creating a third image of said x-rayed blade.

19. The method of claim 16, wherein said matter is residual ceramic core particles.

20. The method of claim 9, wherein the matter is residual ceramic core particles.

* * * * *